(12) United States Patent
Jansson et al.

(10) Patent No.: US 11,480,682 B2
(45) Date of Patent: Oct. 25, 2022

(54) OPTICAL REMOTE SENSING SYSTEM FOR DETECTION OF AERIAL AND AQUATIC FAUNA

(71) Applicant: FaunaPhotonics Agriculture & Environmental A/S, Copenhagen (DK)

(72) Inventors: Samuel Peter Jansson, Lund (SE); Mikkel Brydegaard Sørensen, Lund (SE)

(73) Assignee: FaunaPhotonics Agriculture & Environmental A/S

( * ) Notice: Subject to any disclaimer, the term of this patent is extended or adjusted under 35 U.S.C. 154(b) by 848 days.

(21) Appl. No.: 16/346,322

(22) PCT Filed: Oct. 30, 2017

(86) PCT No.: PCT/EP2017/077809
§ 371 (c)(1),
(2) Date: Apr. 30, 2019

(87) PCT Pub. No.: WO2018/078166
PCT Pub. Date: May 3, 2018

(65) Prior Publication Data
US 2019/0302265 A1    Oct. 3, 2019

(30) Foreign Application Priority Data

Oct. 31, 2016    (EP) ...................... 16196659

(51) Int. Cl.
*G01S 17/88*    (2006.01)
*G01S 7/48*    (2006.01)
(Continued)

(52) U.S. Cl.
CPC ............. *G01S 17/88* (2013.01); *A01K 29/00* (2013.01); *A01M 1/026* (2013.01);
(Continued)

(58) Field of Classification Search
CPC ..... A01K 29/00; A01K 67/033; A01M 1/026; A01M 31/002; G01S 7/4802;
(Continued)

(56) References Cited

U.S. PATENT DOCUMENTS 7,450,171 B2 *    11/2008    Ide .................... G03B 13/30
                                                                  348/349
2010/0171835 A1 *    7/2010    Kasai .................. G01N 21/3581
                                                                  348/E5.085
(Continued)

FOREIGN PATENT DOCUMENTS

WO    WO 2016/148768 A1    9/2016

OTHER PUBLICATIONS

International Search Report and Written Opinion of International Searching Authority for Application No. PCT/EP2017/077809, dated Jan. 26, 2018 (3 pages).
(Continued)

*Primary Examiner* — Sang H Nguyen
(74) *Attorney, Agent, or Firm* — Nixon Peabody LLP

(57) ABSTRACT

A method for determination of a distance from an observation reference point to an object in a measurement volume that can be utilized in a passive optical remote sensing system, and optical remote sensing systems that utilizes the method.

12 Claims, 10 Drawing Sheets

(51) Int. Cl.
  *G01S 17/08* (2006.01)
  *G01S 7/481* (2006.01)
  *A01M 31/00* (2006.01)
  *A01M 1/02* (2006.01)
  *A01K 29/00* (2006.01)
  *G01S 17/46* (2006.01)

(52) U.S. Cl.
  CPC ............ *A01M 31/002* (2013.01); *G01S 7/481* (2013.01); *G01S 7/4802* (2013.01); *G01S 7/4816* (2013.01); *G01S 17/08* (2013.01); *G01S 17/46* (2013.01)

(58) Field of Classification Search
  CPC ........ G01S 7/4816; G01S 7/481; G01S 17/46; G01S 17/08; G01S 17/88
  See application file for complete search history.

(56) References Cited

U.S. PATENT DOCUMENTS

| | | | | |
|---|---|---|---|---|
| 2011/0311132 | A1* | 12/2011 | Meimoun | A61B 3/1015 382/162 |
| 2012/0199655 | A1* | 8/2012 | Fukuba | G06K 7/10811 235/455 |
| 2014/0168484 | A1* | 6/2014 | Suzuki | H04N 5/232122 348/246 |

OTHER PUBLICATIONS

Brydegaard, M. et al., "Super Resolution Laser Radar with Blinking Atmospheric Particles—Application to Interacting Flying Insects"; Progress in Electromagnetics Research, vol. 1347, pp. 141-151, Jan. 1, 2014; XP055368766 (11 pages).

Malmqvist, E. et al., "Effective Parameterization of Laser Radar Observations of Atmospheric Fauna"; IEEE Journal of Selected Topics in Quantum Electronics, IEEE Service Center, Piscataway, NJ; vol. 22, No. 3, pp. 1-8; May 1, 2018; XP011603985 (8 pages).

Gebru, A. et al., "Investigation of atmospheric insect wing-beat frequencies and iridescence features using a multispectral kHz remote detection system"; Society of Photo-Optical Instrumentation Engineers, Journal of Applied Remote Sensing, vol. 8, No. 1, pp. 083503-1-083503-14; Jan. 1, 2014; XP060047078 (15 pages).

Gebru, A. et al., "Probing insect backscatter cross-section and melanization using kHz optical remote detection system"; SPIE—International Society for Optical Engineering, Proceedings, vol. 9975, pp. 997504-1997504-17; Sep. 19, 2016; XP060076640 (17 pages).

Brydegaard, M. et al.; "Insect monitoring with fuorescence lidar techniques: feasibility study"; Applied Optics, Optical Society of America; vol. 48, No. 30, pp. 5668-5677; XP001549326 (10 pages).

Liang, M. et al.; "Continuous-wave differential absorption lidar"; Laser & Photonics Reviews, vol. 9, No. 6, pp. 629-636; Oct. 29, 2015; XP055368959 (8 pages).

Brydegaard, M. et al.; "Towards Quantitative Optical Cross Sections in Entomological Laser Radar—Potential of Temporal and Spherical Parameterizations for Identifying Atmospheric Fauna"; PLoS One 10(8); e0135231; DOI 10.1371/joumal.pone.0135231; Aug. 21, 2015 (15 pages).

* cited by examiner

OPTICAL REMOTE SENSING SYSTEM FOR DETECTION OF AERIAL AND AQUATIC FAUNA

CROSS-REFERENCE TO RELATED APPLICATIONS

This application is a U.S. National Stage of International Application No. PCT/EP2017/077809, filed Oct. 30, 2017, which claims the benefit of European Patent Application No. 16196659.3, filed Oct. 31, 2016, both of which are incorporated herein by reference in their entireties.

FIELD

The present invention relates to optical remote sensing systems, both passive systems with no source for emission of electromagnetic radiation and active systems comprising one or more sources of electromagnetic radiation, e.g. used in the field for detection of aerial and aquatic fauna.

BACKGROUND

Aerial fauna comprises insects that play a crucial role in the earth's ecosystem and influence mankind in multiple ways; e.g. acting as pollinators for food production, as pests that can have a devastating effect on agriculture and as mosquitoes and biting midges that can transmit deadly diseases to humans and livestock.

To study insects, the traditional method is using traps in which insects are caught for subsequent inspection and analysis. Various types of traps are used and the trap method has for decades been the preferred method for entomologists to retrieve insect information, such as species, gender, age classification, micromorphology, and dietary information. The method, however, is highly laborious, time-consuming and costly per insect. Hence, the numbers of insects that can be studied are limited to the number of insects that may be trapped (typically in the single to tens, or low hundreds), the available resources (man-power), or the accessibility of the area/atmospheric region of interest. Furthermore, many trapping methods are known to be biased and perturbed (Muirhead-Thomson R, Trap responses of flying insects: The influence of trap design on capture efficiency, Academic Press (1991)).

To overcome the limitations of traditional traps, LIDAR (Light Detection And Ranging) systems have been proposed, see for example Brydegaard Sørensen, Mikkel L U; Guan, Zuguang L U; Wellenreuther, Maren L U and Svanberg, Sune L U (2009) In Applied Optics 48 (30). p. 5668-5677. Such LIDAR systems for aerial fauna have been the subject of significant research and comprise a laser beam that is transmitted into the atmosphere and a receiver/detector that measures the backscattered laser light from insects. The systems are capable of counting the number events, where an insect intersects with the laser beam. Due to the long range and scanning possibility of laser beam, large atmospheric regions may be analysed for aerial fauna. Hence, the systems are capable of counting a large number of insects, such as in the tens to hundreds of thousands, and even up to millions.

SUMMARY

A new method is provided for determination of a position of an object in a measurement volume. The new method can be utilized in a simple passive optical remote sensing system with no source for emission of electromagnetic radiation, e.g. detecting scattered sunlight, and optical remote sensing systems are provided that utilize the method.

The object may be any particle that is small in comparison with the measurement volume so that the particle can interact with electromagnetic radiation in the measurement volume as a point scatterer or approximately as a point scatterer, i.e. the particle can be considered to constitute one localized scattering centre, or approximately one localized scattering centre, that scatters electromagnetic radiation in the measurement volume.

The object may be a living organism forming part of aerial fauna, such as invertebrates, insects, etc.; or forming part of aquatic fauna, such as algae, plankton, argulus, plants, fungi, flagellates, corals, etc.

Thus, an optical remote sensing system is provided, e.g. for analysing fauna, comprising an optical system, a detector array, and a signal processor, wherein the optical system is configured for reception of electromagnetic radiation from a measurement volume, wherein the electromagnetic radiation includes electromagnetic radiation having interacted with an object moving through the measurement volume along a trajectory, i.e. the path that the moving object follows through the measurement volume as a function of time, and wherein the detector array comprises individual detector elements, each of which provides an output signal in response to received electromagnetic radiation incident upon it, and wherein the optical system and the detector array are arranged with relation to each other so that the optical system directs the received electromagnetic radiation onto the individual detector elements of the detector array, and wherein the signal processor is adapted for determination of a position of the object in the measurement volume based on a difference in time, such as a time lag or time delay, between two, or at least two, of the output signals provided by respective individual detector elements of the detector array in response to received electromagnetic radiation incident upon the respective detector elements and having interacted with the object moving through the measurement volume along the trajectory.

For example, the signal processor may be adapted for determination of a position of the object in the measurement volume based on a difference in time, such as a time lag or time delay, between two, or at least two, of the output signals provided by respective adjacent individual detector elements of the detector array in response to received electromagnetic radiation incident upon the respective detector elements and having interacted with the object moving through the measurement volume along the trajectory.

The position may be determined as a distance from the optical system to the object in the measurement volume, e.g. a distance between an observation reference point at an optical element of the optical system and the object in the measurement volume, e.g. with the object located at a centre of the part of the trajectory located inside the measurement volume.

The signal processor may be adapted for determination of the difference in time based on cross-correlation of the two, or at least two, of the output signals provided by the detector elements of the detector array in response to electromagnetic radiation incident upon the respective detector elements and having interacted with the object moving through the measurement volume along the trajectory.

An optical axis of the optical system is an imaginary line that defines a path along which light propagates through the optical system. For an optical system composed of simple lenses and mirrors, the optical axis passes through the centre of curvature of each lens or mirror surface, and coincides with an axis of rotational symmetry.

Preferably, a centre of the detector array is aligned with the optical axis, i.e. for an imaginary light source positioned at the centre of the detector array for emission of a light beam in the direction of the optical axis, the (imaginary) light beam will propagate through the optical system and the measurement volume along the optical axis of the optical system.

Preferably, the detector array is positioned with relation to the optical axis so that the detector elements are arranged symmetrically with relation to the optical axis of the optical system.

The field of view of a detector is a solid angle through which a detector is sensitive to electromagnetic radiation.

The optical system may be an image forming system and may image an object plane onto an image plane aligned with the detector array. In the following this object plane is denoted the object plane of the detector array.

Each of the detector elements of the detector array has an individual field of view which is a part of the field of view of the detector array. At the object plane of the detector array, each of the detector elements has a separate field of view that does not overlap with the field of view of another detector element of the detector array. At a distance from the object plane of the detector array towards the optical system, the fields of view of respective detector elements do overlap. The overlap increases with distance to the object plane of the detector array.

In other words, the object plane of the detector array is focused on the detector array. If an imaginary plane is moved from the object plane of the detector array towards the detector array, the image at the detector array of that plane gets more and more de-focused with increased distance to the object plane of the detector array.

When an object moves through the measurement volume, the object will enter the field of view of different detector elements with different timing and thus, there will be a difference in time between the output signals of different detector elements in response to received electromagnetic radiation having interacted with the object moving through the measurement volume. The difference in time will depend on the overlap of field of views, i.e. the amount of de-focus, of the respective detector elements and thereby with position of the object along the length of the measurement volume.

The optical remote sensing system may comprise a dark cavity, also denoted a termination, positioned within a field of view of the detector array, thereby defining an end of the measurement volume.

The dark cavity may be a container with an opening and black inner walls for absorption of electromagnetic radiation. The opening may be aligned with the field of view of the detector array of the optical remote sensing system so that reception of background electromagnetic radiation by the optical remote sensing system is minimized.

The measurement volume is a volume from which the detector array may receive electromagnetic radiation having interacted with an object residing in the measurement volume.

Typically, the measurement volume is evenly illuminated, typically by sunlight, and the measurement volume may be delimited by a dark cavity at one end and an aperture of the optical system at another end and by the field of view of the detector array between the two ends.

The measurement volume may be illuminated with one or more artificial light sources, such as lamps, e.g. ceiling mounted lamps for illumination of indoor measurement volumes, and lasers, e.g. diode lasers, arrays of diode lasers, supercontinuum sources, etc., for illumination of indoor and outdoor measurement volumes.

Throughout the present disclosure, electromagnetic radiation is said to be received by the optical system when the electromagnetic radiation is incident upon optical elements of the optical system and directed towards the detector array.

The optical system may comprise an optical element that can direct and make the received electromagnetic radiation converge towards the detector array, such as a focussing lens, a focussing mirror, a Fresnel lens, a diffractive optical element, etc.

Preferably, the object plane and the image plane of the optical system are perpendicular to the optical axis of the optical system.

The object plane of the detector array may be located at infinity.

The object plane of the detector array may coincide with the end of the measurement volume.

The optical remote sensing system may comprise a telescope for reception of electromagnetic radiation from the measurement volume and for directing the received electromagnetic radiation towards the detector array for detection.

The telescope may be a reflecting telescope, such as a Newtonian telescope, a Cassegrain telescope, etc., or a refracting telescope, such as a Galilean telescope, a Keplerian telescope, etc.

Regarding the size of an image produced by an imaging system of an object extending across and having the size of the field of view of the imaging system, such as a telescope or lens, the image will be small when the object is close to the imaging system and the image will be large when the object is far from the imaging system, the object being moved along the optical axis of the system.

Throughout the present disclosure, near field is where the image of the object is smaller than the aperture of the imaging system, whereas far field is where the image of the object is larger than the aperture of the imaging system. At a certain distance between near field and far field the image of the object has the same size as the aperture of the imaging system. This distance is the limit between the near field and the far field.

Preferably, the object plane of the detector array coincides with the limit between a near field and a far field of the optical system.

The optical remote sensing system may comprise additional detectors, e.g. discrete detectors with a single detector element and/or detector arrays, e.g. for detection of electromagnetic radiation of different wavelength ranges or of different polarizations.

The detector array may comprise a quadrant detector, i.e. a detector with four detector elements arranged in two rows and two columns that are perpendicular to each other.

The detector array and possible additional detectors may be made of Silicon (Si), Indium Gallium arsenide (InGaAs), etc. For example, the Silicium quadrant detector S4349 and/or the InGaAs quadrant detector G6849 made by Hamamatsu may be used as the detector array in the new optical remote sensing system.

In an optical remote sensing system with one or more further discrete detectors and/or detector arrays, one or more dichroic beam splitters may be used to direct different parts of the electromagnetic radiation towards respective different detectors.

The signal processor may further be adapted for determination of a parameter of the received electromagnetic radiation relating to the object in the measurement volume based on at least one output signal provided by the detector array and/or another detector of the system in response to received electromagnetic radiation, i.e. electromagnetic radiation incident upon it, having interacted with the object.

For example, the signal processor may be adapted for determination of direction of movement of the object through the measurement volume based on at least two of the output signals provided by respective detector elements of the detector array in response to received electromagnetic radiation, i.e. electromagnetic radiation incident upon the respective detector elements, having interacted with the object.

Further, the signal processor may be adapted for counting the number of objects.

The amount of scattered light from an insect and its modulation include information on body size, wing-beat frequency, spectral information (in the optical domain) of specific molecules (such as melanin, wax, chitin or haemoglobin), microstructures, such as wing membrane thickness, etc., etc.

The signal processor may be adapted for extracting such information for each object, e.g. for species identification.

For example, a dichroic beam splitter adapted to transmit SWIR electromagnetic radiation (wavelength range from 1400 nm to 3000 nm) and reflect NIR electromagnetic radiation (wavelength range from 750 nm to 1400 nm) may be positioned in front of two detector arrays, namely a Si quadrant detector for detection of electromagnetic radiation ranging from 0.19 µm to 1 µm; and an InGaAs quadrant detector for detection of electromagnetic radiation ranging from 0.9 µm to 1.7 µm. These detectors are also capable of resolving wing-beat frequency provided that the sampling frequency is adjusted to be suitable for recording the fundamental wing-beat frequency and preferably also higher harmonics of the wing-beat frequency, e.g. sampling frequencies ranging from 10 Hz to 50 kHz. The fundamental wing-beat frequency of some insects is at most 1 kHz.

Objects have been simulated in a raytracing model of the measurement volume and the following equations have been devised based on the simulation.

The signal processor may be adapted for calculation of the distance or range $\hat{r}$ from the optical system, e.g. from an observation reference point at an optical element of the optical system, e.g. a centre of a focussing mirror or a centre of a focussing refractive lens of the optical system, to the object in the measurement volume from the equation:

$$\hat{r} = \frac{\tau \phi_{tel} f}{\tau\left(\frac{\phi_{tel} f}{r_o} - d_s\right) + \Delta t \frac{d_s}{2}} \quad (1)$$

wherein:
$\phi_{tel}$ is the aperture of the optical system,
f is the focal length of the optical system,
$d_s$ is the width of the detector array,
$r_o$ is the distance between the observation reference point of the optical system and the object plane of the detector array at the optical axis of the system,
$\Delta t$ is the time duration of the object event, i.e. the time the object moving through the measurement volume spends within the measurement volume, and $\tau$ is the difference in time between the at least two of the output signals response to electromagnetic radiation incident upon the respective detector elements and having interacted with the object moving through the measurement volume along the trajectory, e.g. determined by cross-correlation of the output signals of the respective individual detector elements.

An object event denotes a time period during which an object resides within the measurement volume.

The accuracy of equation (1) depends on relations between dimensions of the measurement volume with relation to parameters of the optical system. When the object plane of the detector array coincides with the limit between the near field and far field, the width of the measurement volume is constant along the longitudinal direction of the measurement volume, and the determination accuracy is independent of the distance between the optical system and the object in the measurement volume. When the object plane of the detector array is located in the near field, the measurement volume converges and the equation becomes less accurate at close range and more accurate at far range, whereas if the object plane of the detector array is located in the far field, the equation is more accurate at close range and less accurate at far range.

By rearranging equation (1) and introducing the parameter $d_f$, which is the width of the field of view of the detector array in its object plane, and $$\alpha = \frac{\phi_{tel}}{d_f},$$

which is the inverse of the linear scaling coefficient of the measurement volume with the distance $\hat{r}$ to the optical system, equation (1) can be rewritten as equation (2):

$$\frac{\hat{r}}{r_o} = \frac{\alpha \frac{2\tau}{\Delta t}}{(\alpha - 1)\frac{2\tau}{\Delta t} + 1} \quad (2)$$

As mentioned above, if the detector array is focused at the limit between the near field and far field $r_f$, the measurement volume maintains a constant width along its longitudinal direction. In other words, if $r_o = r_f$, then $d_f = \phi_{tel}$ and $\alpha = 1$ so that $$\frac{\hat{r}}{r_o} = \frac{2\tau}{\Delta t} \quad (3)$$

and at $\hat{r} = 0$, $\tau = 0$ and at $\hat{r} = r_0$, $\tau = \Delta t/2$ and $\tau/\Delta t$ is a linear function of $\hat{r}$ between 0 at $\hat{r} = 0$ and ½ at $\hat{r} = r_0$.

In equation (2), $\hat{r}$ depends on the quotient $\tau/\Delta t$. $\tau$ and $\Delta t$ are both proportional to the velocity of the object moving through the measurement volume so that the determination of $\hat{r}$ is independent of the velocity and independent of the shape of the measurement volume cross-section. For example, both circular and quadratic detector arrays and apertures can be utilized without affecting the accuracy of the determination of $\hat{r}$.

The determination of $\hat{r}$ is independent of altitude of a horizontal trajectory of movement through the measurement volume. The angle of the trajectory with relation to the optical axis of the optical system, i.e. heading angle, and with relation to horizontal, i.e. the pitch, can affect the accuracy of the determination of r̂.

Some, or all, of the detector elements of the detector array may be positioned along an image of a horizontal trajectory through the measurement volume.

Some, or all, of the detector elements of the detector array may be positioned along an image of a vertical trajectory through the measurement volume.

The optical remote sensing system may comprise at least one source of electromagnetic radiation that is adapted for emission of electromagnetic radiation towards the measurement volume for illumination of the object in the measurement volume.

The at least one source of electromagnetic radiation may comprise one or more lasers for emission of respective one or more beams of electromagnetic radiation.

The at least one source of electromagnetic radiation may emit radiation in the Near-Infrared (NIR) range, i.e. having wavelengths ranging from 750 nm to 1400 nm.

The at least one source of electromagnetic radiation may emit radiation in the Short-Wavelength Infrared (SWIR) range, having wavelengths ranging from 1400 nm to 3000 nm.

The at least one source of electromagnetic radiation may comprise two separate continuous wave (CW) lasers.

The at least one source of electromagnetic radiation may comprise a diode laser, an array of diode lasers, a supercontinuum source, etc. A supercontinuum source may be obtained from commercial vendors, such as Eagleyard Photonics GmbH or NKT Photonics A/S.

The optical remote sensing system may comprise one or more beam shapers, each of which is adapted for shaping the intensity profile of a respective laser beam into a desired profile, such as a Gaussian intensity profile, at top hat intensity profile, etc.

The one or more beam shapers may comprise an optical fibre adapted for shaping the intensity profile of the beam into a Gaussian beam profile.

The one or more beam shapers may comprise a phase contrast system adapted for shaping the intensity profile of the beam, such as a Gaussian intensity profile, at top hat intensity profile, etc.

The signal processor may be adapted for controlling the at least one source of electromagnetic radiation and for turning the at least one source of electromagnetic radiation on and off alternatingly.

The signal processor may be adapted for determination of background emission of electromagnetic radiation from the measurement volume when the at least one source of electromagnetic radiation is turned off.

The optical remote sensing system may comprise a frame for supporting various parts of the optical remote sensing system, including a first housing for accommodation of the optical system and possibly the detector array.

The frame may further support a second housing for accommodation of the at least one source of electromagnetic radiation.

The frame may comprise a beam, e.g., of aluminium.

The first housing may be mounted to the beam.

The second housing may be mounted to the beam.

The optical remote sensing system may comprise at least one camera arranged for monitoring of the measurement volume.

The at least one camera may comprise at least one line scan camera.

The optical remote sensing system may comprise at least one third housing for accommodation of the at least one camera and may be mounted to the frame.

The optical remote sensing system may be portable.

The optical remote sensing system may be suitable for outdoor and/or indoor measurements.

The signal processor may be connected to the at least one camera for reception of images from the at least one camera.

The signal processor may be adapted for performing image analysis of images received from the at least one camera.

The signal processor may be adapted for controlling the at least one source of electromagnetic radiation in response to the performed analysis.

The signal processor may be adapted for performing image analysis of images received from the at least one camera for monitoring alignment of the at least one source of electromagnetic radiation and the detector array.

The signal processor may be adapted for monitoring alignment of the at least one source of electromagnetic radiation and the detector array based on the at least one output from the detector array without an animal in the measurement volume.

The signal processor may be adapted for monitoring obstacles residing in a volume traversed by the electromagnetic radiation emitted by the at least one source of electromagnetic radiation.

The signal processor may be adapted for turning the at least one source of electromagnetic radiation off to prevent inadvertent illumination of objects.

The optical remote sensing system may comprise a scanner that is arranged for moving the frame, e.g. pan and/or tilt and/or pitch and/or traverse the frame, and thereby moving the measurement volume.

The signal processor may be adapted for controlling the scanner to move the measurement volume to scan a desired volume along a desired moving trajectory, e.g. to perform measurements throughout the desired volume larger than the measurement volume; or to perform measurements in sample volumes, e.g. in a regular pattern of volumes separated by volumes wherein no measurements are performed.

The optical remote sensing system may comprise a calibrator arranged for placing an object with a known optical characteristic in the measurement volume.

The signal processor may be adapted to determine data based on electromagnetic radiation received from the object in the measurement volume.

The optical remote sensing system may comprise a bandpass filter cooperating with the detector array for suppression of background signals and having a centre wavelength within the wavelength range of the detector array.

The optical remote sensing system may comprise one or more additional bandpass filters cooperating with respective optional additional detectors and/or detector arrays for suppression of background signals and having a centre wavelength within the wavelength range of the respective additional detectors and/or detector arrays.

Scattering processes from insects involve diffuse and specular reflectance. Specular reflection could come from the body or the wing depending on the type of species and nature of the body and wing of the insect. If an insect has a furry body and shiny wing or the opposite, the total scatter cross-section will be a combination of diffuse and specular reflections. This can be decomposed into different components to identify the body and wing contributions. In general, specular and diffuse reflectance contributes to the total optical cross-section OCS. The specular reflectance from the wing is responsible for the higher order harmonics.

In an optical remote sensing system with detection of more than one wavelength, chromatic properties of animals in the measurement volume may be determined.

Also iridescence features can be determined, e.g. by comparing the shape of temporal waveforms of received electromagnetic radiation in the visible range VIS with electromagnetic radiation in the near infrared range NIR.

Also melanisation properties can be determined, e.g. by comparing OCS of insects in the NIR and SWIR ranges, since the optical cross-section ratio between NIR and SWIR scales with melanisation.

Determination of insect size is significantly more accurate in the SWIR range as compared to NIR, since NIR OCS depends on the extent of melanisation of the insect, while SWIR OCS is relatively insensitive to insect melanisation.

Melanin is a natural pigment or chromophore that determines the colour of an insect's body and wings. Melanisation gives rise to dark or brownish appearance in the VIS. This is due to multiple reflections of the incident light interaction with the tissue. This effect could introduce some uncertainty in determining absolute optical cross-section OCS of insects in the Ultraviolet (UV), VIS and NIR. SWIR is insensitive to melanisation. Considering the difference between NIR and SWIR, reflectance from insects of different colour and same size could be different depending on which detector used or detection wavelength chosen. Other colouration mechanisms than melanisation exist in the VIS and UV, such as cryptic coloration, warning colour, sexually selected colours, structural colours, etc. These effects have little impact in the NIR, and therefore melanisation is preferably determined from the ratio of OCS, e.g. back scattered OCS, in the two bands NIR and SWIR rather than from the ratio of OCS in the two bands VIS and SWIR.

Melanisation may be calculated according to the following equation:

$$\text{Melanisation} = 1 - [OCS_{NIR}/(OCS_{SWIR} + OCS_{NIR})]$$

wherein
$OCS_{NIR}$ and $OCS_{SWIR}$ are the OCS in the NIR and SWIR ranges, respectively.

The body and wing contribution of the insect to the total OCS may be distinguished using a sliding temporal minimum filter with width of wing-beat periodicity and determine the peak value of the sliding minimum and thereby define the non-oscillatory body contribution to the total OCS.

With high frequency, wing-beat modulation as well as higher order harmonics may be resolved, e.g. by calculation of the modulation power spectrum that includes the non-oscillating body contribution of the insect observation in the measurement volume, the fundamental wing-beat frequency and its harmonics overtones. The fundamental frequency may be estimated from the median value of the distance between the peaks in the power spectrum. The relative strength of the odd and even harmonics may be used for the determination of observed orientation of the insect and ultimately the direction of movement, i.e. the flight direction. Insects appears large twice during one wing-beat cycle (strong 2ω) from the side and appear large once during one wing-beat cycle (strong 1ω) according the insect model. This means that the total OCS oscillates depending on the type of insect and the observed orientation of the insect.

The optical remote sensing system can be utilized to improve and/or reduce use of pesticides and chemicals in agriculture and aquaculture productions. In particular, the optical remote sensing system can be utilized to quantify aerial insect fauna associated with land use, farming regimes and crop type in agricultural landscapes, and for pest control, and for information in relation to pollinators.

The optical remote sensing system can be utilized for control, warning and/or combat of vector-borne diseases, such as malaria, yellow fever, zika virus, HAT and AAT sleeping sickness, Chikungunya virus, Dengue fever, West Nile virus, etc.

The optical remote sensing system may be used in agronomics. Agricultural intensification and pesticide use has profound effects on aerial ecology. However, impact on the composition of aerial fauna is not well understood given limitations in monitoring technologies.

Advantageously, the optical remote sensing system or method is used, e.g. for smart farming, precision agriculture, integrated pest management, environmental impact assessment, smart curtailment, etc., e.g. at a farm or similar to reduce the use of a pesticide and/or agricultural chemical in crops compared to prior year's use of these. By prior years, is meant the yearly average use of a pesticide and/or agricultural chemical over a period of 1 year, alternatively over 3, 5 or 10 years.

A method is provided for optimizing use of pesticides in agriculture. The method comprises the steps of measuring one, two or more species of insects using the optical remote sensing system, analyse data from the measurement and determined a desired pesticide, spraying time, spraying schedule and/or spraying amount.

A method is provided for optimizing use of agricultural chemicals. The method comprises the steps of measuring one, two or more species of insects using the optical remote sensing system, analyse data from the measurement and determined a desired agricultural chemical, spraying time, spraying schedule and/or spraying amount. Preferably, the method is automatic and further comprises a database of insect and pesticide and/or agricultural chemical information for determination of spraying parameters (for example pesticide, chemical, amount, time, or schedule).

Advantageously, the optical remote sensing system is used to exchange measurement data with digital pest and disease modelling platforms.

Advantageously, the optical remote sensing system may be used in malaria control. Today a major limitation in monitoring malaria mosquitoes is that insect abundance assessment is based on insect traps. Placing and emptying the traps are tedious operations and constitute a major effort, and the results are biased with respect to the species, sexes and age groups caught.

The optical remote sensing system may be used for malaria mosquito surveillance and enables non-intrusive on site monitoring of malaria mosquitoes improving decision support for national malaria control programs.

Advantageously, the optical remote sensing system may be used in bird and bat detection at windmill parks. A challenging task in bird monitoring lies in identifying high-altitude migrating bird species and genders.

The optical remote sensing system may be used by windmill park operators in order to determine critical times of operation and/or times for operational stop.

Advantageously, the optical remote sensing system may be used for developers of windmill parks prior to determining the optimum sites of operation, whereby information of migrating birds and or endangered bats can be taken into account.

Advantageously, the optical remote sensing system may be used in aquatic applications, e.g. fish farming. Aquaculture production systems may suffer from undesired aquatic organisms, such as sea lice and carpulus. An increasing problem is chemical treatments to reduce fish diseases, excessive antibiotic use and resistance. This has negative environmental impact, such algae bloom, marine mammal deaths, marine debris, and waste on the ocean floor.

Advantageously, the optical remote sensing system provides a new tool for analysing aquatic organisms and may be used to reduce the use of chemicals in fish farms and aquaculture production.

Advantageously, the optical remote sensing system may be used for monitoring of vegetation/seafloor via fluorescence of chlorophyll.

With the optical remote sensing system and method improved determinations of specificity of insects are performed in-situ.

Improved optical remote sensing systems and methods are provided for measuring, quantifying, monitoring, classifying, specifying, surveying, predicting, forecasting, investigating, and/or warning of aerial and/or aquatic fauna, e.g. for use in a number of fields and applications, such as agronomics, malaria control, windmill parks, aquaculture production (e.g. fish farms), and science (e.g. entomology, ornithology, biogeography, oceanography).

The signal processor of the new optical remote sensing system may be constituted by dedicated hardware or may be performed in a signal processor programmed for this purpose, or performed in a combination of dedicated hardware and one or more signal processors.

As used herein, the term "signal processor" is intended to refer to CPU-related entities, either hardware, a combination of hardware and software, software, or software in execution. The term signal processor may also refer to any integrated circuit that includes a CPU and possibly additional hardware, which may not be a CPU-related entity.

For example, a "signal processor" may be, but is not limited to being, a process running on a processor, a processor, an object, an executable file, a thread of execution, and/or a program.

By way of illustration, the term "signal processor" designates both an application running on a processor and a hardware processor. One or more "signal processors" may reside within a process and/or thread of execution, and one or more "signal processors" may be localized on one hardware processor, possibly in combination with other hardware circuitry, and/or distributed between two or more hardware processors, possibly in combination with other hardware circuitry.

Also, a signal processor may be any component or any combination of components that is capable of performing signal processing. For examples, the signal processor may be an ASIC processor, a FPGA processor, a general purpose processor, a microprocessor, a circuit component, or an integrated circuit.

BRIEF DESCRIPTION OF THE DRAWINGS

The drawings illustrate the design and utility of embodiments of the new optical remote sensing system, in which similar elements are referred to by common reference numerals. These drawings are not necessarily drawn to scale. In order to better appreciate how the above-recited and other advantages and objects are obtained, a more particular description of the embodiments will be rendered, which are illustrated in the accompanying drawings. These drawings depict only typical embodiments and are not therefore to be considered limiting of its scope.

In the drawings.

DETAILED DESCRIPTION

Figure 1:
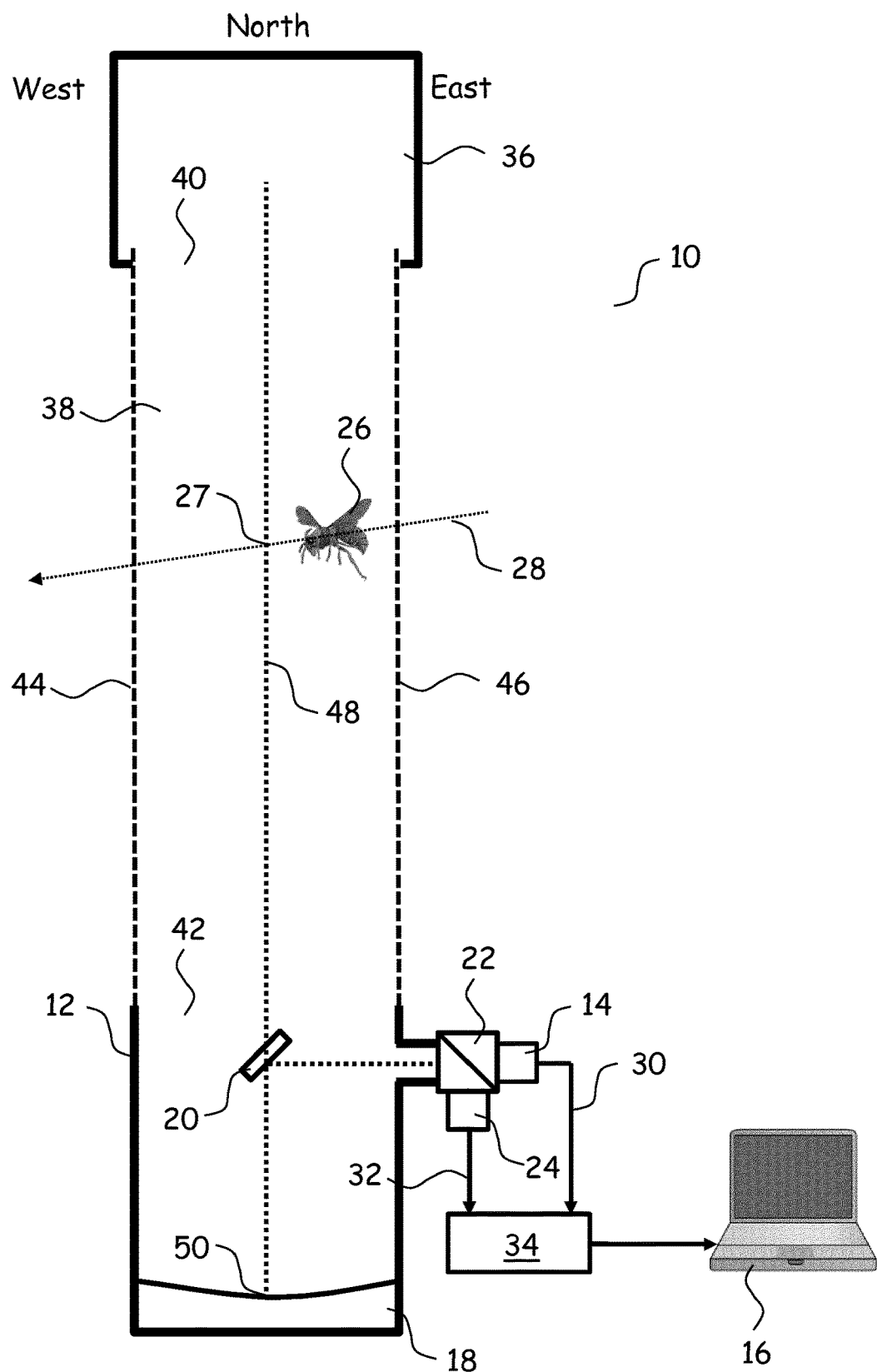
FIG. 1 schematically illustrates a remote sensing system with a Newtonian telescope, FIG. 2 a) schematically illustrates a front view of a Newtonian aperture, FIG. 2 b) schematically illustrates in a cross-section seen from above light rays incident on different detector elements of the detector array, FIG. 2 c) illustrates ray tracing of the field of view of two adjacent detector elements, FIG. 2 d) shows simulated signals from two adjacent detector elements in response to a particle traversing the measurement volume perpendicular to its length at different distances.

Various exemplary embodiments are described hereinafter with reference to the figures. It should be noted that the figures are not drawn to scale and that elements of similar structures or functions are represented by like reference numerals throughout the figures. It should also be noted that the figures are only intended to facilitate the description of the embodiments. They are not intended as an exhaustive description of the optical remote sensing systems and method according to the appended claims or as a limitation on the scope of the claims. In addition, an illustrated embodiment needs not have all the aspects or advantages shown. An aspect or an advantage described in conjunction with a particular embodiment is not necessarily limited to that embodiment and can be practiced in any other embodiments even if not so illustrated, or not so explicitly described.

The optical remote sensing system and corresponding methods will now be described more fully hereinafter with reference to the accompanying drawings, in which various types of the optical remote sensing system are shown. The optical remote sensing system may be embodied in different forms not shown in the accompanying drawings and should not be construed as limited to the embodiments and examples set forth herein. For example, the new method is illustrated for a passive optical remote sensing system relying on natural illumination of objects in the measurement volume; however, the method is equally applicable in active optical remote sensing systems comprising one or more sources of electromagnetic radiation for illumination of objects in the measurement volume.

Passive optical remote sensing systems are desirable, since they are very affordable compared to active systems. Typically, they are mobile and simpler to employ, with no concerns for eye-safety since they rely on sunlight or moonlight as their illumination source, and they have much reduced energy consumption compared to their active counterparts.

Drawbacks are that they perform suboptimal without direct sunlight or moonlight, and that there are constraints for the orientation of the measurement volume. For example, with an optical remote sensing system with a telescope, the telescope is preferably pointed towards north on the Northern Hemisphere and towards south on the Southern Hemisphere in order to operate in the preferred backscatter mode.

In the following, the new method is disclosed in connection with a Newtonian telescope in cooperation with a quadrant detector positioned in the image plane of the Newtonian telescope as schematically illustrated in FIG. 1.

FIG. 1 schematically illustrates an optical remote sensing system 10 for analysing fauna, comprising an optical system 12, a detector array 14, and a signal processor 16.

The optical system 12 is a Newtonian telescope 12 with a primary mirror 18 and a secondary mirror 20, wherein the primary mirror 18 and the secondary mirror 20 cooperate to direct received electromagnetic radiation, i.e. electromagnetic radiation incident on the primary mirror 18, from a measurement volume 38 onto the detector array 14 via the beam splitter 22.

The beam splitter 22 is a dichroic beam splitter 22 positioned in front of the detector array 14, which is a Si quadrant detector 14 for detection of electromagnetic radiation ranging from 0.19 μm to 1 μm, and in front of an InGaAs detector 24 for detection of electromagnetic radiation ranging from 0.9 μm to 1.7 μm. The dichroic beam splitter 22 is adapted to transmit SWIR electromagnetic radiation and reflect NIR electromagnetic radiation. These detectors 14, 24 are also capable of resolving wing-beat frequency provided that the sampling frequency is adjusted to be suitable for recording the fundamental wing-beat frequency and preferably also higher harmonics, e.g. sampling frequencies ranging from 10 Hz to 50 kHz. The fundamental wing-beat frequency of some insects is at most 1 kHz.

The dichroic beam splitter 22 and the InGaAs detector 24 are optional and not required for the illustrated optical remote sensing system 10 to operate according to the new method that is further explained below.

When an object 26, such as an insect, moves through the measurement volume along a trajectory 28, the electromagnetic radiation having interacted with the object 26 moving through the measurement volume, is received by the optical system 12, i.e. in the illustrated system 10 the Newtonian telescope.

Figure 2:
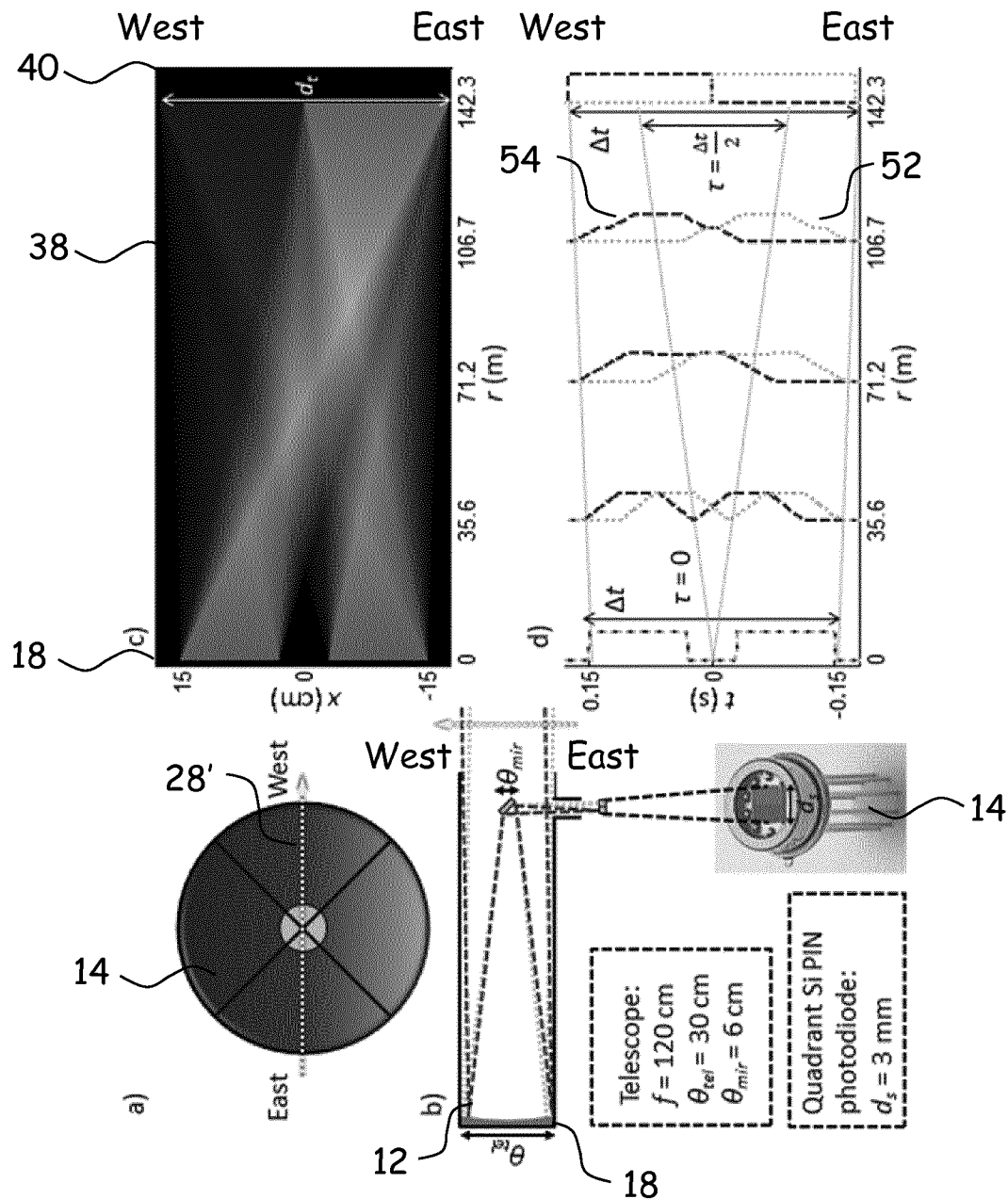

The Si quadrant detector 14 comprises four detector elements as shown in more detail in FIG. 2 a), each of which provides an output signal in response to electromagnetic radiation incident upon it. The four output signals 30 of the Si quadrant detector 14 and the output signal 32 of the InGaAS detector 24 are connected to a sampling unit 34 that samples and digitizes the output signals with a 20 kHz sampling frequency and transfers the sampled signals to the signal processor 16 of a laptop computer for further processing.

Alternatively, the signal processor 16 may be realized in an integrated circuit, e.g. housed together with the detector array 14, so that the optical remote sensing system 10 may output data on various parameters of objects moving through the measurement volume 38, such as the determined position, direction of movement, wing-beat frequency, etc.

The optical remote sensing system 10 comprises a dark cavity 36, also denoted a termination 36, positioned within the field of view of the Newtonian telescope 12 and defines an end of the measurement volume 38. The illustrated dark cavity 36 is a container with an opening 40 and black inner walls for absorption of electromagnetic radiation. The opening 40 is aligned with the field of view of the detector array 14 of the Newtonian telescope 12 so that reception of background electromagnetic radiation by the telescope 12 is minimized.

The measurement volume 38 is the volume defined by the field of view FOV of the detector array 14 of the telescope 12 indicated by dashed lines 44, 46 between the aperture 42 of the telescope 12 and the opening 40 of the dark cavity 36. In the following, the measurement volume 38 is assumed to be evenly illuminated by sunlight.

The measurement volume 38 is an elongated volume typically several hundred meters long with a diameter of, e.g., 30 cm.

The telescope 12 is focussed at the opening 40 of the dark cavity 36, whereby the object plane of the detector array 14 coincides with the opening 40 of the dark cavity 36 so that an image of the dark cavity 36 is focussed onto the detector array 14. The dotted line 48 indicates the optical axis 48 of the telescope 12.

The signal processor 16 is adapted for determination of a distance from an observation reference point, which in FIG. 1 is defined as the centre 50 of the primary mirror 18 of the telescope 12, to the object 26 in the measurement volume 38, i.e. to a centre 27 of the trajectory 28, based on at least two of the output signals 30 provided by the detector array 14, i.e. the Si quadrant detector 14, in response to received electromagnetic radiation having interacted with the object 26. This is further explained below with reference to FIG. 2.

For example, the signal processor 16 may be adapted for determination of the distance to the object 26 in the measurement volume 38 based on cross-correlation of at least two of the output signals 30 produced by the detector elements of the detector array 14 in response to received electromagnetic radiation having interacted with the object.

In the illustrated optical remote sensing system 10, the signal processor 16 is adapted for calculation of the distance $\hat{r}$ from the centre 50 of the primary mirror 18 to the object 26, i.e. to a centre 27 of the trajectory 28, in the measurement volume 38 using the equation:

$$\hat{r} = \frac{\tau \phi_{tel} f}{\tau \left( \frac{\phi_{tel} f}{r_o} - d_s \right) + \Delta t \frac{d_s}{2}} \quad (1)$$

wherein:
$\phi_{tel}$ is the telescope aperture,
f is the telescope focal length,
$d_s$ is the width of the detector array,
$r_o$ is the distance between the observation reference point and the object plane 36 of the detector array 14,
$\Delta t$ is the time duration of object events, and
$\tau$ is the difference in time between the at least two of the output signals provided by the respective detector elements of the detector array in response to received electromagnetic radiation having interacted with the object moving through the measurement volume along the trajectory, e.g. determined by cross-correlation of the output signals of the respective detector elements.

Obviously, if the observation reference point is moved away from the centre 50 of the primary mirror 18 by a distance $d_{ref}$ that is positive when the observation reference point is moved towards the measurement volume, the distance $\hat{r}$ from the displaced observation reference point is calculated using the equation:

$$\hat{r} = \frac{\tau \phi_{tel} f}{\tau \left( \frac{\phi_{tel} f}{r_o} - d_s \right) + \Delta t \frac{d_s}{2}} - d_{ref}$$

Insects are simulated in a raytracing model of the measurement volume 38 and the ranging equation is devised based on the simulation.

The signal processor 16 is further be adapted for determination of direction of movement of the object 26 through the measurement volume 38 based on at least two of the output signals 30 provided the detector elements of the Si quadrant detector 14 in response to received electromagnetic radiation having interacted with the object 26.

The signal processor 16 is also adapted for determination of a parameter of the received electromagnetic radiation relating to the object 26 in the measurement volume 38 based on at least one output signal 30, 32 provided by a detector 14, 24 of the system 10 in response to received electromagnetic radiation having interacted with the object 26, e.g. based on at least one of the output signals 30 provided by the detector elements of the detector array 14 in response to received electromagnetic radiation having interacted with the object 26.

For example, in addition to counting a number of objects 26, the signal processor 16 is adapted to extract characteristic data for insects moving through the measurement volume 38, such as wing-beat oscillations, spherical scattering coefficient (size), spectral information (in the optical domain) of specific molecules (such as melanin, wax, chitin or haemoglobin), and also of microstructures such as wing membrane thickness.

As illustrated in FIG. 2 a), two of the detector elements of the Si quadrant detector 14 are positioned along an image of a horizontal centre trajectory through the measurement volume 38 at the opening 40 of the dark cavity 36, and two other of the detector elements of the detector array 14 are positioned along an image of a vertical centre trajectory through the measurement volume 38 at the opening 40 of the dark cavity 36.

The optical remote sensing system 10 may comprise a frame (not shown) for supporting the telescope 12 with the detectors 14, 24 and possibly the sampling unit 34.

The illustrated optical remote sensing system 10 is portable.

The optical remote sensing system 10 may comprise a scanner (not shown) that is arranged for moving the frame, e.g. pan and/or tilt and/or pitch and/or traverse the frame, and thereby moving the measurement volume 38.

The signal processor 16 may be adapted for controlling the scanner (not shown) to move the measurement volume 38 to scan a desired volume along a desired moving trajectory, e.g. to perform measurements throughout the desired volume larger than the measurement volume 38; or to perform measurements in sample volumes, e.g. in a regular pattern of volumes separated by volumes wherein no measurements are performed.

The optical remote sensing system 10 may comprise a calibrator (not shown) arranged for placing an object 26 with a known optical characteristic in the measurement volume 38.

The optical remote sensing system 10 may comprise a bandpass filter (not shown) cooperating with the detector array 14 for suppression of background signals and having a centre wavelength within the wavelength range of the detector array 14.

The optical remote sensing system 10 may comprise an additional bandpass filter (not shown) cooperating with the optional additional detector 24 for suppression of background signals and having a centre wavelength within the wavelength range of the detector 24.

Utilization of the new method is further illustrated in FIG. 2.

FIG. 1 a) schematically shows a top view of the Si quadrant detector 14a as mounted to the Newtonian telescope 12 and the dotted arrow 28' indicates a trace of electromagnetic radiation having interacted with the insect 26 in the measurement volume 38 and impinging on the detector elements of the Si quadrant detector 14a. In the illustrated example and as indicated by the arrow, the insect moves horizontally from east to west through the measurement volume 38, and the electromagnetic radiation impinges on the detector element labelled East first and subsequently impinges on the detector element labelled West. Examples of output signals produced by the detector elements in response to the impinging electromagnetic radiation are shown in FIG. 2 d) as further explained below.

FIG. 2 b) illustrates from above how the two adjacent detector elements labelled East and West, respectively, of the Si quadrant detector 14 receive electromagnetic radiation from slightly different directions through the telescope 12.

FIG. 2 c) illustrates raytracing of the measurement volume 38 of the two adjacent detector elements labelled East and West, respectively. In the upper half of the measurement volume 38, the field of view of the eastern detector element is pale grey and the field of view of the western detector element is dark grey. In the lower half of the measurement volume 38, overlapping fields-of-view are pale grey. The detector array 14, i.e. the Si quadrant detector 14, is focused at the opening 40 of the dark cavity 36 that minimizes reception of background light. Thus, the detector array 14 is de-focussed at the aperture 42 and gradually gets more and more focused along the measurement volume 38 towards the opening 40 that is aligned with the object plane of the detector array 14, of the dark cavity 36. In other words, the field of view of each individual detector element the Si quadrant detector 14 overlaps completely with the other detector element field of views at the aperture 42 of the telescope 12, and the field of views are gradually separated with increased distance to the aperture 42 and at the opening 40 of the dark cavity 36, they are completely separated as the image of the detector element is in focus at the opening 40.

FIG. 2 d) shows examples of simulated output signals produced by the detector elements in response to the impinging electromagnetic radiation as a point scatter moves through the measurement volume 38 horizontally from east to west and perpendicular to the optical axis 48 at a speed of 1 m/s at different distances to the Newtonian telescope 12. The pale grey dotted lines show signals from the detector element labelled East in FIG. 2 a), and the dark grey dotted lines show signals from the detector element labelled West in FIG. 2 a).

Parameters r, τ, and Δt are also shown in FIG. 2 d).

According to the new method, the distance to the object 26 moving through the measurement volume 38 can be calculated from the parameters listed below, four of which are related to the new optical remote sensing system 10, and two of which are related to signals produced by detector elements.

Figure 3:
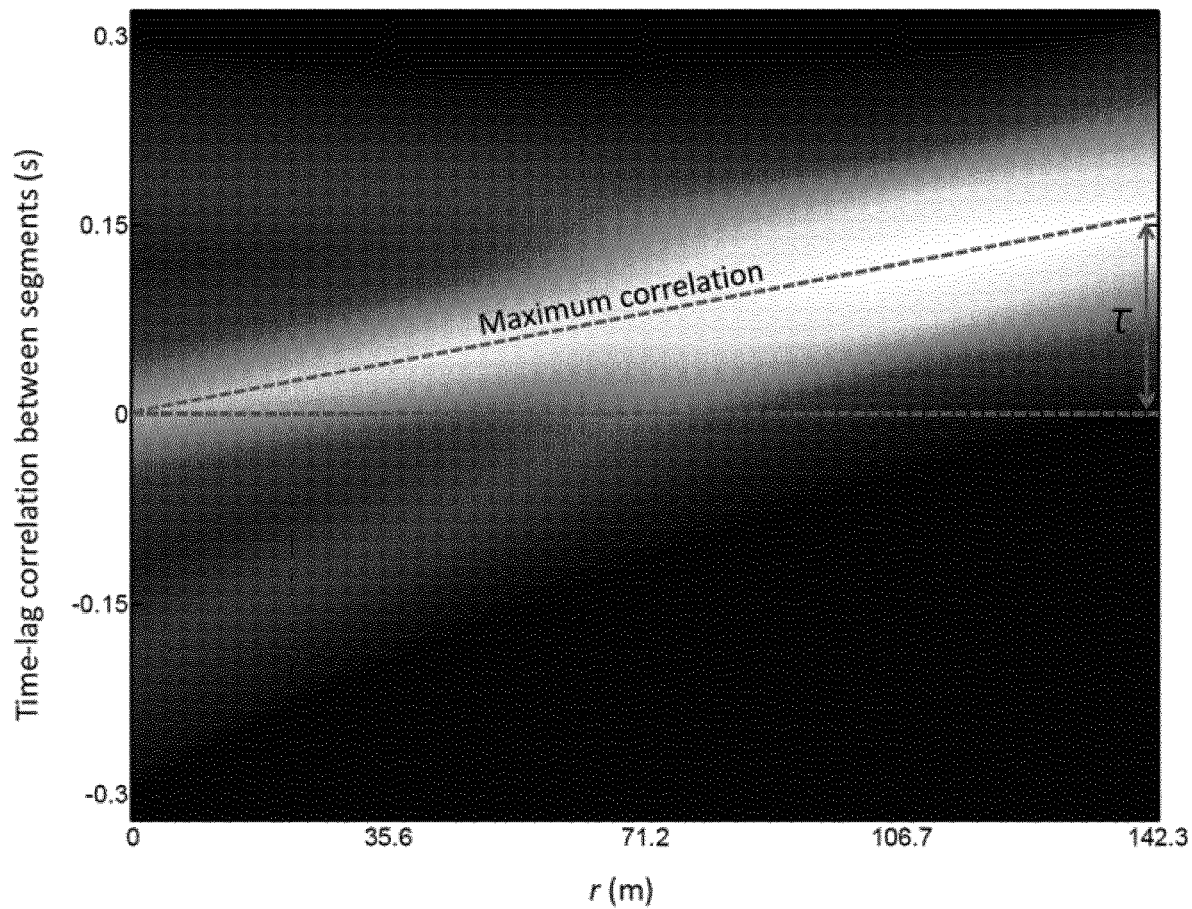
FIG. 3 illustrates east—west time lag correlation of the raytracing of FIG. 2 c)

Δt is the transit time, i.e. the time it takes for the object to move through the measurement volume 38. Δt can be determined as part of the parameterization process disclosed in: E. Malmqvist, S. Jansson, S. Török, and M. Brydegaard, "Effective Parameterization of Laser Radar Observations of Atmospheric Fauna," IEEE Journal of Selected Topics in Quantum Electronics, vol. 22, pp. 1-8, 2016.

τ is the difference in time, i.e. the time lag, between the output signals produced by two respective adjacent detector segments, and is extracted through time lag correlation of the signals. This corresponds to determining the time lag between the signals that yields the highest correlation, i.e. where the signals are the most similar. The east-west time lag correlation of the entire raytracing field in FIG. 2 c) is shown in FIG. 3.

FIG. 2: East-west time lag correlation of the raytracing field from FIG. 2 c). The correlation is at its highest at the time lag where the signals in the eastern and western detector segments are the most similar. Due to the gradual separation of the field of view of the eastern- and western detector segment's with increased distance in the measurement volume 38, τ is a range-dependent parameter that starts out at 0 at close range where the field of view overlap is complete, and ends up at Δt/2 at far range where the field of view separation is complete.

Once these parameters are retrieved from an insect event, they can be inserted into the new ranging equation, equation (1), to calculate the distance between the primary mirror of the telescope and the insect.

$$\hat{r} = \frac{\tau \phi_{tel} f}{\tau \left( \frac{\phi_{tel} f}{r_o} - d_s \right) + \Delta t \frac{d_s}{2}} \quad (1)$$

The validity of equation (1) can be evaluated with the simulated insect signals in the raytracing model, where the distance is known. Extracting τ and Δt from the simulated signals and inserting them into equation (1) yields the results illustrated in FIG. 4.

FIG. 3 is a plot used for evaluation of the new ranging equation, where predicted range $\hat{r}$ is plotted against actual range r. The solid line is a plot of the function y=x. The small deviations arise from the discreet nature of the simulation, and as can be discerned from the plot, the method yields perfect results.

By rearranging equation (1) and introducing the parameter $d_f$, which is the width of the field of view of the Si quadrant detector 14 in its object plane, see FIG. 2 c), and $$\alpha = \frac{\phi_{tel}}{d_f},$$

which is the inverse of the linear scaling coefficient of the measurement volume 38 with r, equation (1) can be rewritten as equation (2):

$$\frac{r}{r_o} = \frac{\alpha \frac{2\tau}{\Delta t}}{(\alpha - 1) \frac{2\tau}{\Delta t} + 1} \quad (2)$$

If the object plane of the detector array lies in the near field, the measurement volume 38 converges, whereas if the object plane of the detector array lies in the far field, the measurement volume 38 diverges. As such there exists a limit between the near field and far field, $r_f$, and if the detector array is focused at this limit between the near field and far field $r_f$, the measurement volume 38 maintains a constant width along its longitudinal direction. In other words, if $r_o=r_f$, then $d_r=\phi_{tel}$. Where one decides to terminate the measurement volume 38 therefore has implications on the properties of the new methods, see FIG. 5. With the parameters from FIG. 2, $r_f$=121.2 m.

Figure 4:
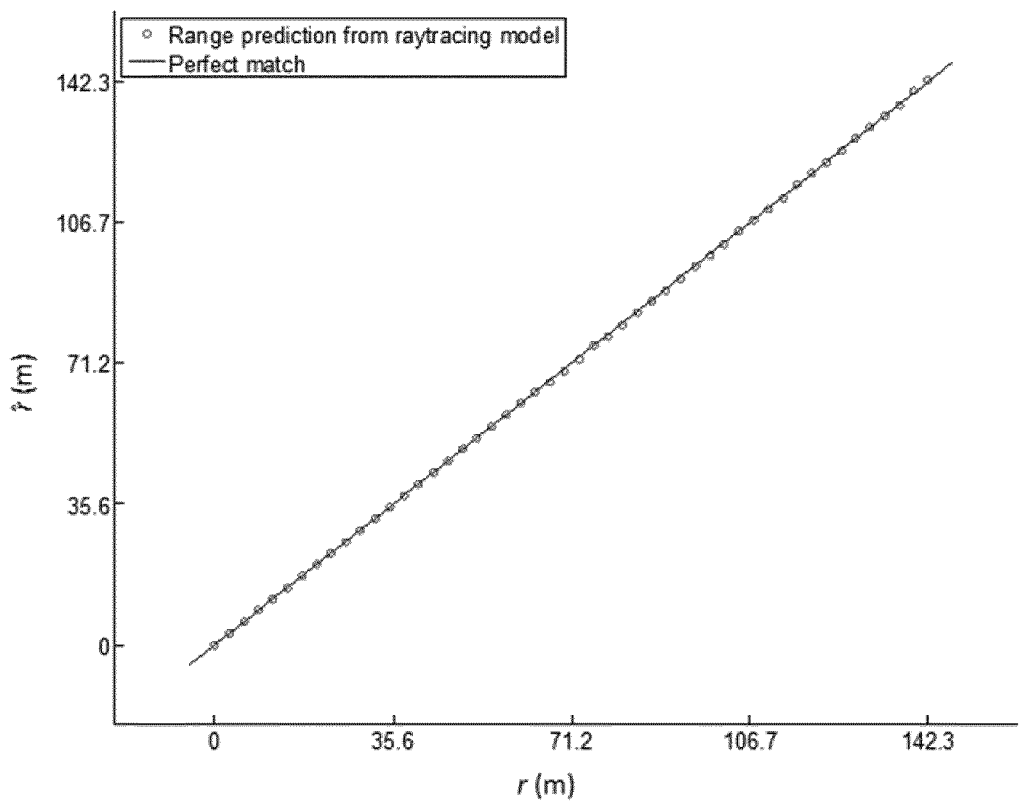
FIG. 4 is a plot of predicted distance as a function of distance determined by ray tracing, FIG. 5 schematically illustrates distance accuracy as a function of distance to the object plane of the detector array.

FIG. 4 illustrates how the properties of the new method changes with dimensions of the measurement volume 38 with relation to parameters of the telescope 12. When the object plane of the detector array 14 coincides with the limit between the near field and far field, i.e. $r_o$ is equal to $r_f$, the width of the measurement volume 38 is constant along the longitudinal direction of the measurement volume 38 and the ranging accuracy is unaffected by the distance between the telescope 12 and the trajectory 28 of the insect 26. When the object plane of the detector array is located in the near field, the measurement volume 38 converges and the method becomes less accurate at close range and more accurate at far range, whereas if the object plane of the detector array is located in the far field, the method is more accurate at close range and less accurate at far range.

Figure 6:
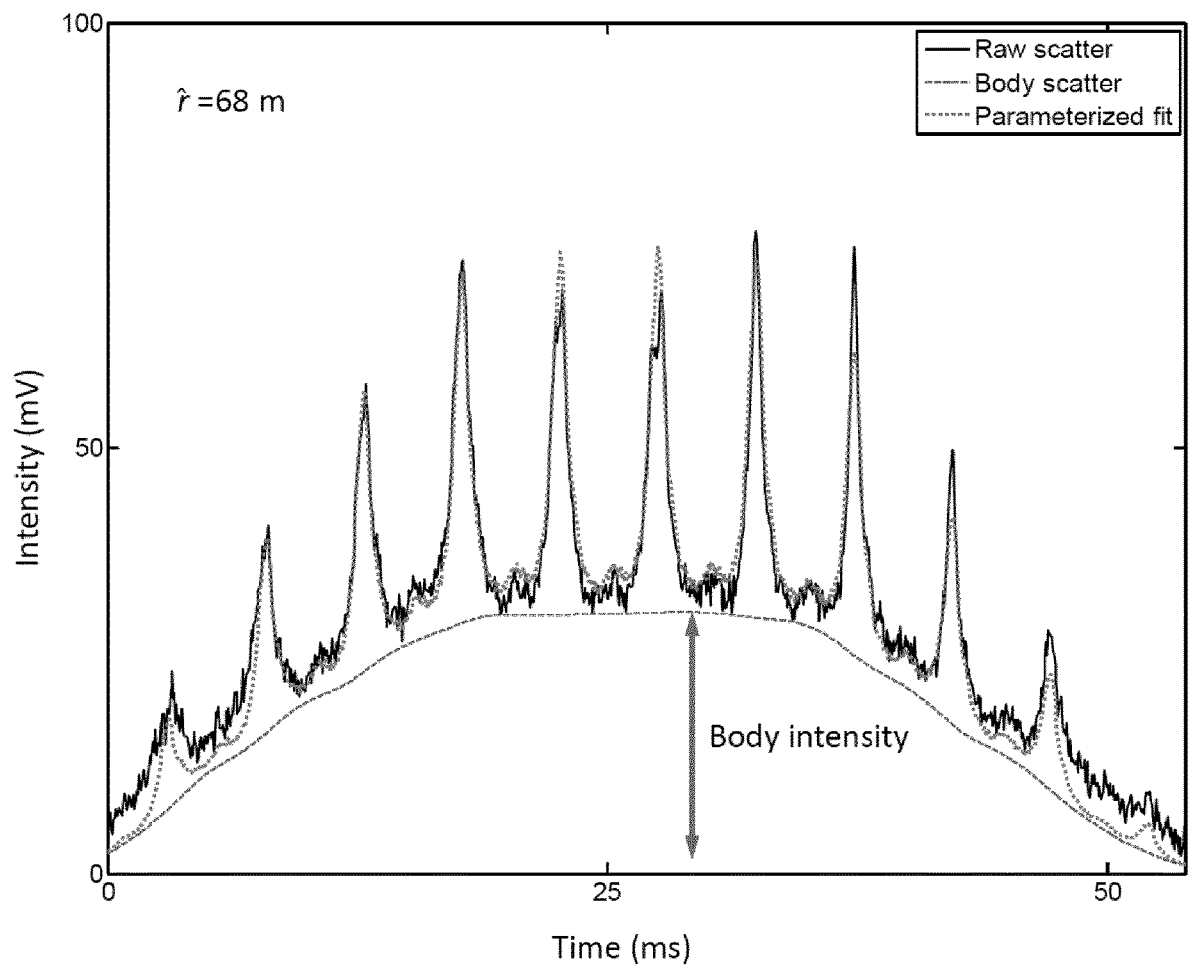
FIG. 6 is a plot of raw and parameterized insect scatter signals.
Figure 7:
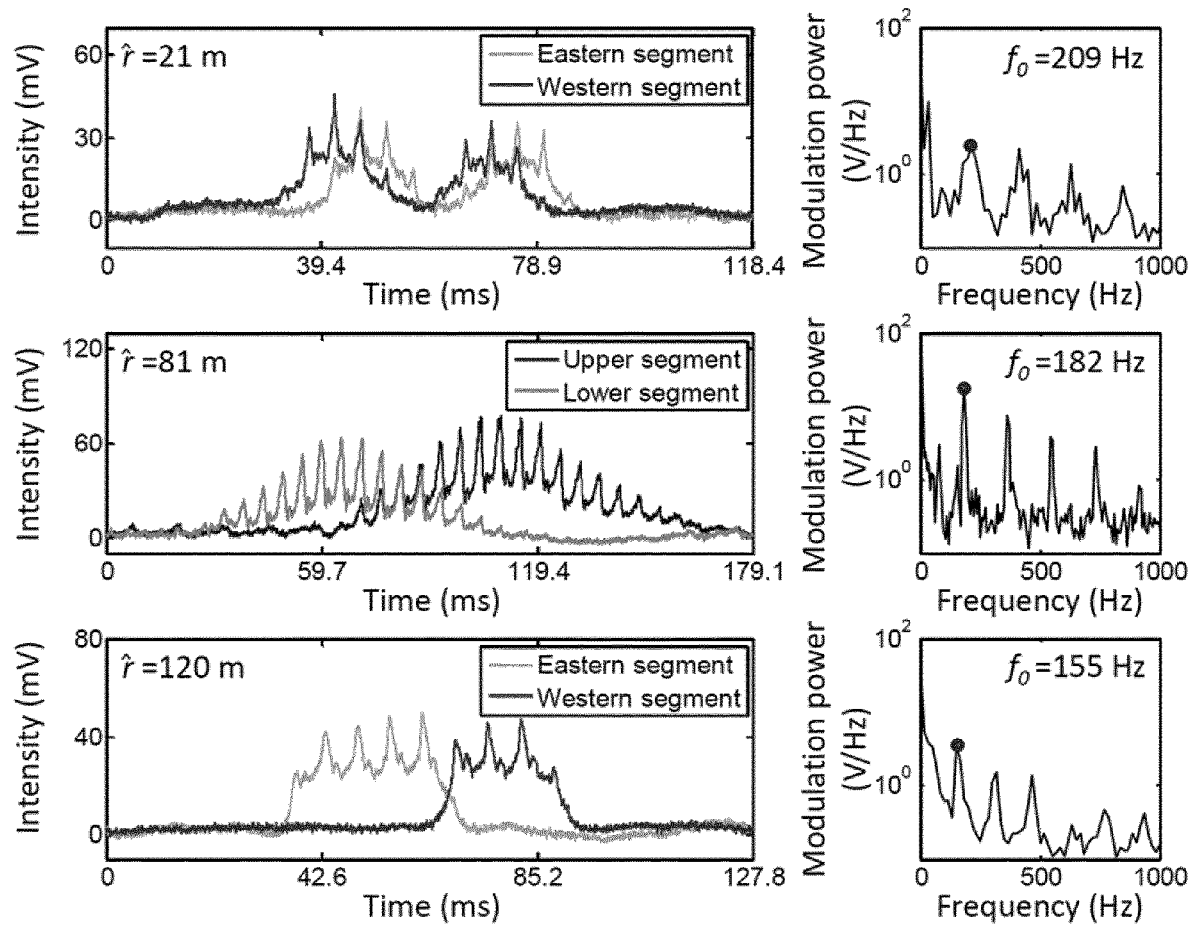
FIG. 7 shows examples of signals from insects flying through the measurement volume.

FIG. 6 shows a detector signal generated in response to an insect moving through the measurement volume 38, together with the body-scatter signal and the result of the parameterization.

Figure 5:
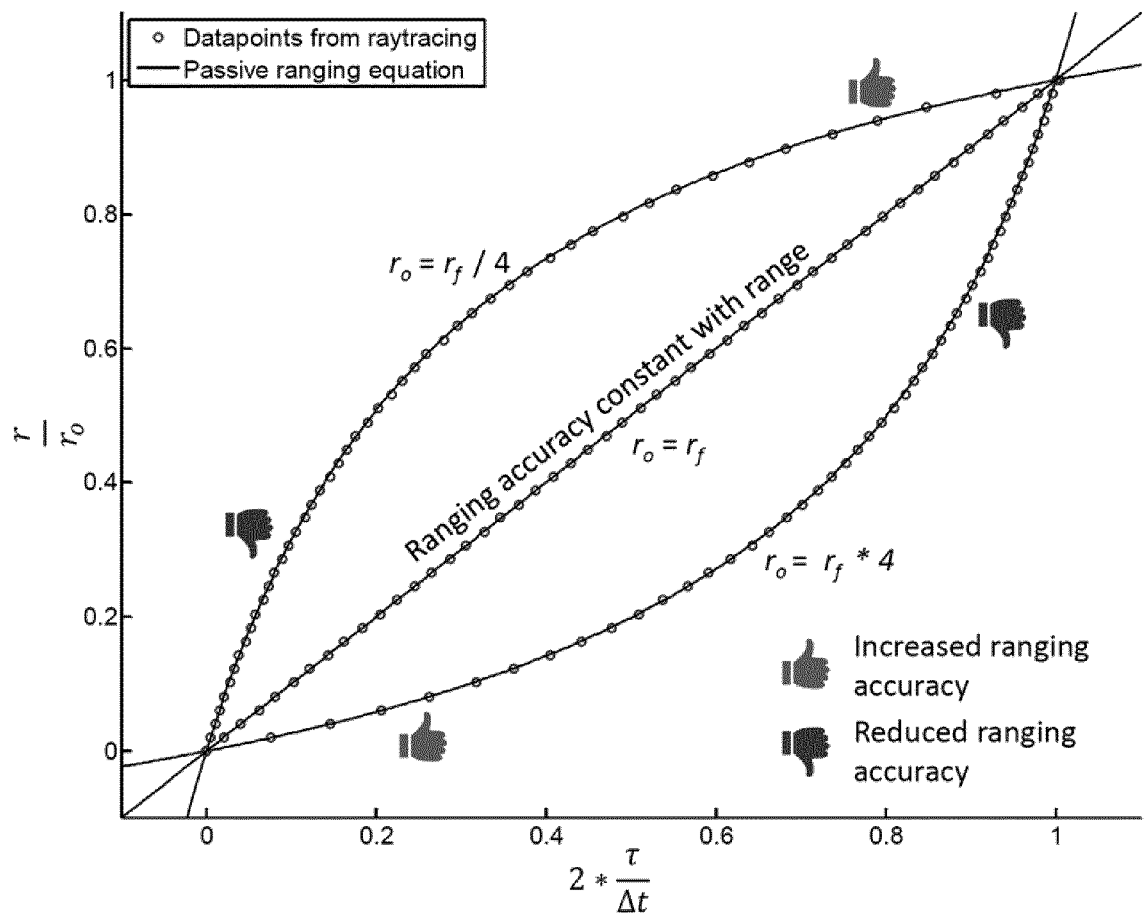

FIG. 5 shows examples of insect event time series and power spectra, from which the ranging parameters τ and Δt, the wing-beat frequency $f_0$, as well as other event parameters have been extracted.

Top: Insect signal with a waveform matching close-range simulation (see FIG. 2 d)). The insect appears in all four detector segments, as expected due to their measurement volume 38 overlapping at close range, and insertion into equation (1) yields a predicted range $\hat{r}$ of 21 m.

Middle: Signal from an insect impinging on the measurement volume 38 at an inclination, appearing in the upper, lower and western detector segments. The waveform matches mid-range simulation, and insertion into equation (1) yields a predicted range $\hat{r}$ of 81 m.

Bottom: Insect signal with a waveform matching far-range simulation, appearing in the eastern, western and upper detector segments. Insertion into equation (1) yields a predicted range $\hat{r}$ of 120 m. The wing-beat frequency $f_0$ is marked in the power spectrum in all three cases.

Through obtaining the body intensity of each observation, the range-dependent sensitivity of the system 10 can be investigated.

Figure 8:
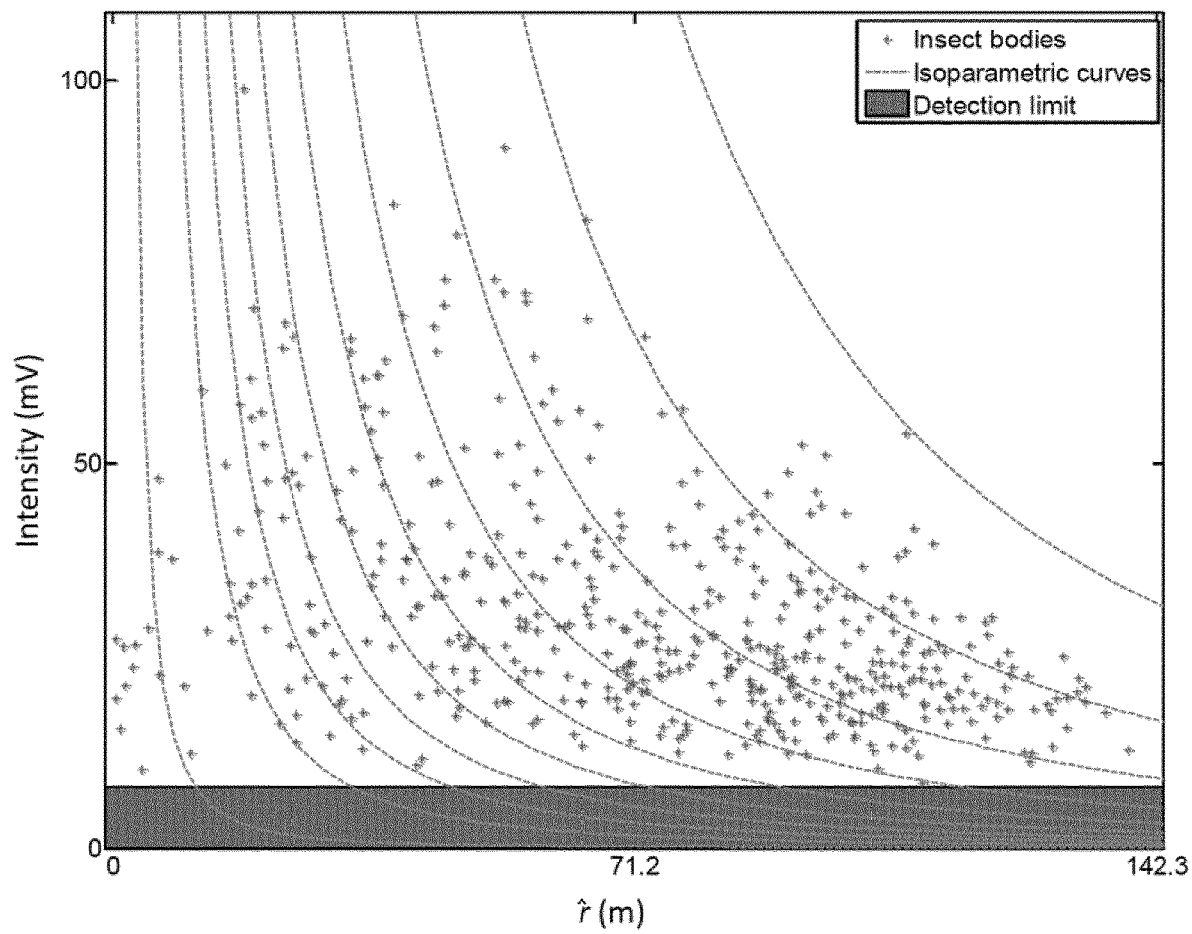
FIG. 8 is a scatterplot of object events against predicted range and body intensity, shown together with iso-parametric curves of the inverse square law and the lower detection limit.

FIG. 8 shows a scatterplot of a large number of events, with predicted range $\hat{r}$ and body intensity of the observations on the axes together with iso-parametric curves of the inverse square law and the lower detection limit.

The body intensity is strongly tied to the heading of insects—if an insect impinges on the measurement volume 38 at a normal angle, it is observed from the side and thus appears large, while if enters at a high incident angle (i.e.

flies along the measurement volume 38) it is observed from the front or back and appears small. In the former case, the insect would also transit the measurement volume 38 quickly, whereas in the latter case it would remain in the measurement volume 38 for an extended period of time. As such, in order to properly evaluate the system sensitivity, the heading angles of insects have to be taken into account. It has been stipulated that the relative strengths of the lower harmonics are tied to the insect heading in relation to the measurement volume 38, and a model has been presented, see M. Brydegaard, "Towards Quantitative Optical Cross Sections in Entomological Laser Radar—Potential of Temporal and Spherical Parameterizations for Identifying Atmospheric Fauna," PLoS ONE, vol. 10, 2015.

On top of being related to the insect heading, the transit time can be used to evaluate the ranging accuracy.

Figure 9:
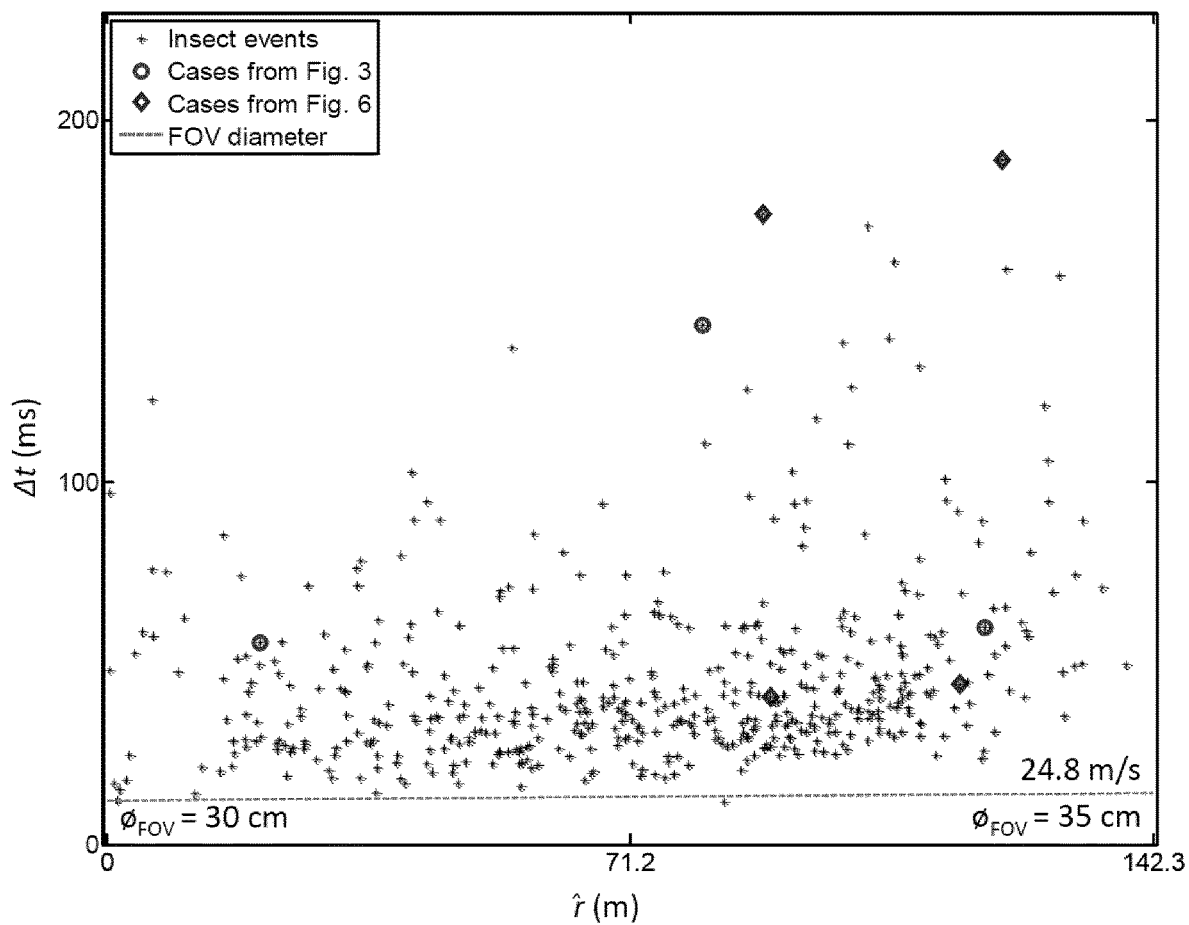
FIG. 9 is a scatterplot of insect events; with predicted range $\hat{r}$ and transit time $\Delta t$ along the axes. Also plotted is a sliding median of the distribution, as well as the diameter of the measurement volume.

FIG. 9 is a scatterplot of insect events; with predicted range $\hat{r}$ and transit time $\Delta t$ on the axes. Also plotted is a sliding median of the distribution, as well as the diameter of the measurement volume 38. As seen in the figure, the transit time increases with predicted range, as is expected due to the diverging measurement volume 38.

On top of the presented method, other useful information related to insect flight in relation to weather and topography and be extracted from quadrant detectors.

Figure 10:
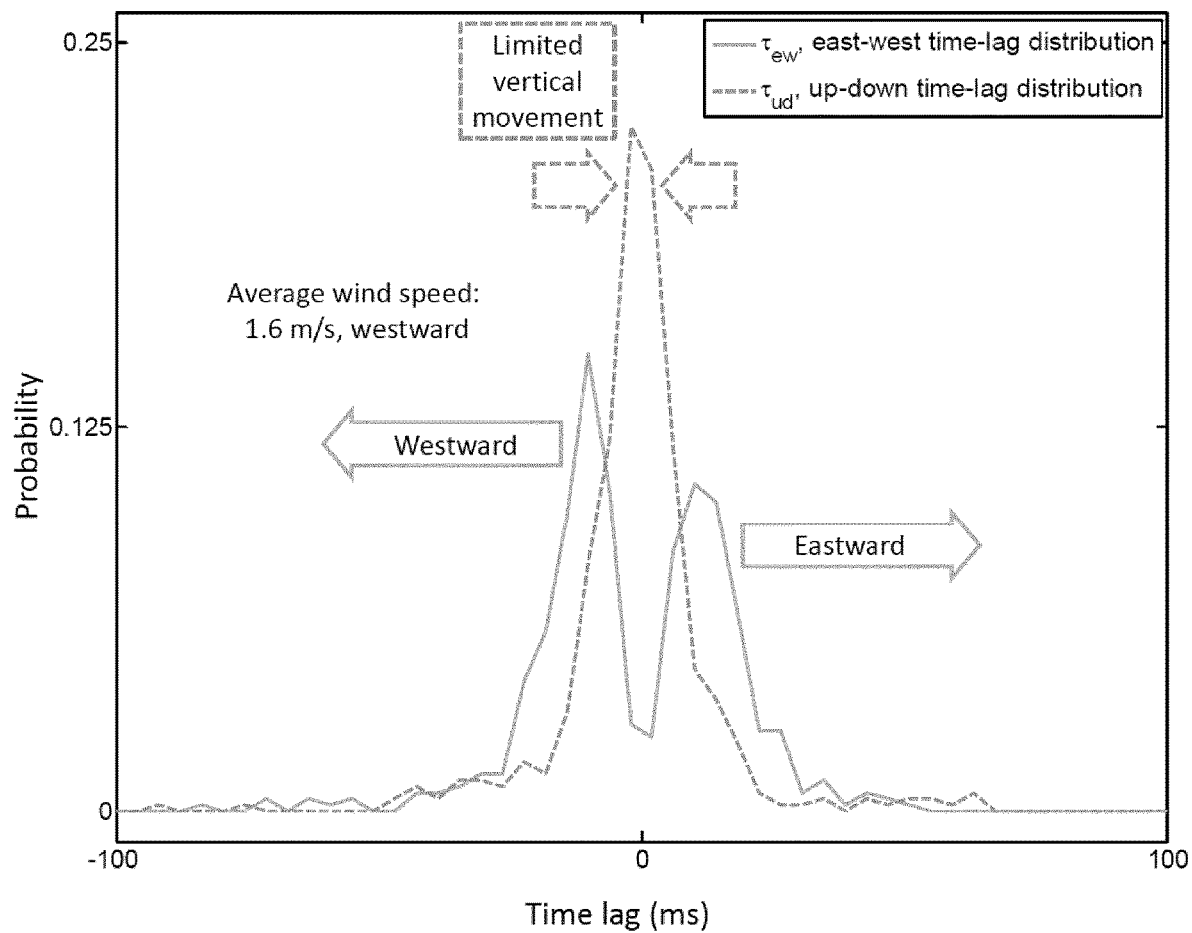
FIG. 10 shows histograms of the east-west and up-down time lags $\tau_{ew}$ and $\tau_{ud}$.

FIG. 10 shows histograms of $\tau_{ew}$ and $\tau_{ud}$, and the average wind speed in direction during the study period is presented. The east-west distribution is bimodal, indicating that the observed insects intersect the measurement volume 38 laterally, while the up-down distribution is single modal and centred around 0, indicating that vertical movement is limited. Throughout the study period, the wind was mostly blowing westward, with an average wind speed of 1.6 m/s. As such, it can be concluded that the insects fly more with than against the wind in this case.

There are a number of possible uses for the presented method. As disclosed herein, it can be implemented horizontally to profile insects in active or passive mode along a transect over the landscape. This implementation requires shielding off of the background, which can be accomplished by aiming the detector into a dark cavity.

By moving into infra-red wavelength regions where the atmosphere does not transmit sunlight, the method can also be implemented vertically, in which case active illumination is required. The method can then be used to monitor migratory fauna, including birds, bats and insects, and through time lag correlation of the detector segments, the direction of movement, i.e. the flight direction, can be obtained. Ideally, the sensor should be focused at the limit between near- and far field, and the setup parameters should be chosen to ensure that this limit ends up at a suitable distance for the study at hand.

Another approach to vertical profiling would be to fix the aim of the setup at the Polaris star, which would ensure sunlight impinging on the measurement volume 38 at an approximately normal angle at all times. The setup could then be implemented vertically in passive mode.

Detection schemes with multiple wavelength- or polarization bands could also be envisioned, by use of dichroic- or polarization beam splitters, and could be implemented in both active and passive remote sensing systems.

Although particular embodiments have been shown and described, it will be understood that they are not intended to limit the claimed inventions, and it will be obvious to those skilled in the art that various changes and modifications may be made without departing from the spirit and scope of the claimed inventions. The specification and drawings are, accordingly, to be regarded in an illustrative rather than restrictive sense. The claimed inventions are intended to cover alternatives, modifications, and equivalents.

With the description above, a person skilled in the art of photonics would be able to carry out the various optical remote sensing systems 10 and methods according to the appended claims. Examples of practical implementation of an optical remote sensing system 10 and data processing can be found in literature, including Mikkel Brydegaard, Aboma Merdasa, Alem Gebru, Hiran Jayaweera, and Sune Svanberg, "Realistic Instrumentation Platform for Active and Passive Optical Remote Sensing," Appl. Spectrosc. 70, 372-385 (2016), included herein by reference, and Brydegaard, M. (2015): "Towards Quantitative Optical Cross Sections in Entomological Laser Radar—Potential of Temporal and Spherical Parameterizations for Identifying Atmospheric Fauna." PLOS ONE, DOI: 10.1371/journal.pone.0135231 also included herein by reference, and Mikkel Brydegaard, Alem Gebru, and Sune Svanberg, "Super Resolution Laser Radar with Blinking Atmospheric Particles—Application to Interacting Flying Insects", Progress In Electromagnetics Research, Vol. 147, 141-151, 2014 also included herein by reference.

The invention claimed is:

1. An optical remote sensing system for analysing fauna, comprising an optical system, a detector array, and a signal processor, wherein the optical system is configured for reception of electromagnetic radiation from a measurement volume, wherein the electromagnetic radiation includes electromagnetic radiation having interacted with an object moving through the measurement volume along a trajectory, and the detector array comprises detector elements, each of which provides an output signal in response to received electromagnetic radiation incident upon it, and wherein the optical system and the detector array are arranged with relation to each other so that the optical system directs the received electromagnetic radiation onto the detector elements of the detector array, wherein an object plane of the detector array is focused on the detector array and coincides with the end of the measurement volume, the signal processor is adapted for determination of a distance from the optical system to the object in the measurement volume based on a difference in time between two of the output signals provided by respective detector elements of the detector array in response to received electromagnetic radiation incident upon the respective detector elements and having interacted with the object moving through the measurement volume along the trajectory and based on a time duration of a time period during which the object resides within the measurement volume.

2. The optical remote sensing system according to claim 1, comprising a dark cavity positioned within a field of view of the optical system thereby defining an end of the measurement volume.

3. The optical remote sensing system according to claim 2, wherein the optical system is adjusted so that an image of the dark cavity is focussed onto the detector array.

4. The optical remote sensing system according to claim 1, wherein the detector array comprises a quadrant detector.

5. The optical remote sensing system according to claim 1, wherein the signal processor is adapted for determination of the difference in time based on cross correlation of the two of the output signals.

6. The optical remote sensing system according to claim 1, wherein the signal processor is adapted for determination of direction of movement of the object through the measurement volume based on the difference in time.

7. The optical remote sensing system according claim 1, wherein the signal processor is adapted to determine the distance from the optical system to the object in the in the measurement volume using the equation:

$$\frac{\hat{r}}{r_o} = \frac{\alpha \frac{2\tau}{\Delta t}}{(\alpha-1)\frac{2\tau}{\Delta t} + 1}$$

wherein: $\hat{r}$ is the distance from the optical system to the object in the measurement volume,
$\alpha$ $$\alpha = \frac{\phi_{tel}}{d_t}$$

is the inverse of the linear scaling coefficient of the measurement volume with the distance r to the optical system, $d_t$, is the width of the field of view of the detector array in its object plane,
$\theta_{tel}$ is the aperture of the optical system,
f is the focal length of the optical system,
$r_o$ is the distance between the optical system and the object plane of the detector array,
$\Delta t$ is the time duration of the object event, and
$\tau$ is the difference in time between the two of the output signals provided by the respective detector elements of the detector array.

8. The optical remote sensing system according to claim 1, wherein detector elements of the detector array are positioned along an image of a horizontal trajectory through the measurement volume.

9. The optical remote sensing system according to claim 1, wherein detector elements of the detector array are positioned along an image of a vertical trajectory through the measurement volume.

10. The optical remote sensing system according to claim 1, wherein the optical system comprises a telescope.

11. The optical remote sensing system according to claim 1, comprising at least one source of electromagnetic radiation that is adapted for emission of electromagnetic radiation towards the measurement volume for illumination of the object in the measurement volume.

12. The optical remote sensing system according to claim 11, wherein the at least one source of electromagnetic radiation comprises a laser for emission of a beam of electromagnetic radiation.

* * * * *